United States Patent [19]
Kitazume et al.

[11] Patent Number: 6,114,544
[45] Date of Patent: Sep. 5, 2000

[54] OPTICALLY ACTIVE FLUORINATED COMPOUNDS

[75] Inventors: Tomoya Kitazume, Tokyo; Takashi Yamazaki, Yokohama; Kenji Mizutani, Yamato, all of Japan

[73] Assignee: Kashima Oil Company, Tokyo, Japan

[21] Appl. No.: 08/470,467

[22] Filed: Jun. 6, 1995

Related U.S. Application Data

[60] Division of application No. 08/164,774, Dec. 10, 1993, which is a continuation-in-part of application No. 07/949,104, Aug. 31, 1992, abandoned.

[30] Foreign Application Priority Data

Jan. 31, 1992 [JP] Japan .................................. 4-015683

[51] Int. Cl.$^7$ .............................. C07D 309/10; C07F 7/02

[52] U.S. Cl. .......................... 549/214; 549/416; 549/417

[58] Field of Search ..................................... 549/214, 416, 549/417

[56] References Cited

PUBLICATIONS

Yamazaki et al., J.C.S., Chem. Comm., 1992, pp. 55–57.

*Primary Examiner*—Joseph McKane
*Assistant Examiner*—Jane C. Oswecki
*Attorney, Agent, or Firm*—Oblon, Spivak, McClelland, Maier & Neustadt, P.C.

[57] ABSTRACT

There is disclosed a novel compound having a fluoromethyl group which itself has a large electron attractive property at an asymmetric carbon atom on a tetrahydropyran ring, which is expected to be a novel type of a liquid crystal.

This novel compound is an optically active fluorinated compound represented by the formula:

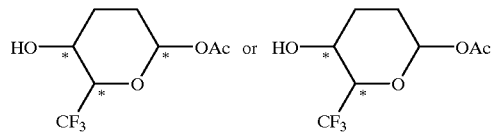

3 Claims, No Drawings

OPTICALLY ACTIVE FLUORINATED COMPOUNDS

This is a Division, of application Ser. No. 08/164,774 filed on Dec. 10, 1993, now allowed which is a Continuation-in-Part of application Ser. No. 07/949,104 filed on Aug. 31, 1992, now abandoned.

BACKGROUND OF THE INVENTION

1. Field of the Invention

The present invention relates to optically active fluorinated compounds, and more specifically it relates to optically active fluorinated compounds useful as raw materials for various chemicals, industrial chemicals, ferroelectric liquid crystals, etc.

2. Description of Related Art

In recent years, liquid crystals have largely been utilized and also the development of liquid crystals having novel structure has been required.

Until now, the research group of the present inventors has succeeded in developing various optically active fluorinated compounds which can be utilized for these liquid crystals (Japanese Patent Applications Laid-Open No. 83074/1989, 163143/1989, 233243/1989, 233244/1989, 49743/1990, 167252/1990, 232208/1990, 232209/1990, etc.).

In such a situation, the present inventors have further intensively studied to develop novel optically active compounds having a tetrahydropyran ring, which are promising as a novel type of liquid crystal.

SUMMARY OF THE INVENTION

An object of the present invention is to provide optically active fluorinated compounds useful as a raw material for ferroelectric liquid crystals.

Another object of the present invention is to provide optically active fluorinated compounds useful for various industrial chemicals such as an enzyme inhibitor, a biologically active substance, an anticancer agent, etc., and further for raw materials of various industrial chemicals.

Specifically, the present invention provides an optically active fluorinated compound represented by the following general formula (I):

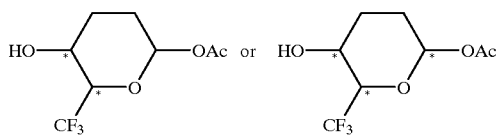

wherein Ac represents an acyl group and * represents an asymmetric carbon atom, and an optically active fluorinated compound represented by the following general formula (II):

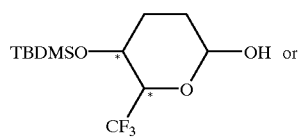

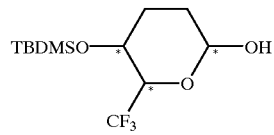

wherein TBDMS represents a t-butyldimethylsilyl group and * has the same meaning as defined above.

PREFERRED EMBODIMENTS OF THE INVENTION

The compound of the general formula (I) according to the present invention can be prepared by various methods, for example, by the following process.

For example, furan is silylated (e.g. trimethylsilylated) to give a compound represented by the general formula (III):

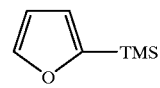

wherein TMS represents a trimethylsilyl group, then the compound is further trifluoroacetylated to give a compound represented by the general formula (IV):

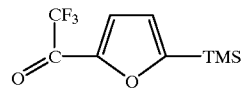

wherein TMS has the same meaning as defined above. The above reaction can be carried out by subjecting to silylation using an organolithium compound such as n-butyl lithium and trimethylsilyl chloride, using a solvent such as tetrahydrofuran and diethyl ether, and then, subjecting to trifluoroacetylation using the above butyl lithium and ethyl trifluoroacetate at a temperature of −78° C. to 0° C.

The resulting compound of the general formula (IV) is reduced according to the conventional method to give a compound represented by the following general formula (V):

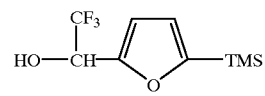

wherein TMS has the same meaning as defined above. The above reaction can be carried out by using a reducing agent such as sodium borohydride, lithium aluminum hydride and stannic chloride.

The compound of the general formula (V) obtained is then acylated by reacting with an acid chloride. Examples of the acid chloride to be used as an acylating agent include acetyl chloride, propionyl chloride, isobutyroyl chloride, octanoyl chloride, benzoyl chloride, etc.

The obtained compound of the following general formula (VI):

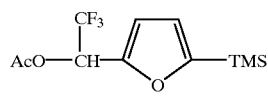

wherein Ac and TMS have the same meanings as defined above, is subjected to asymmetric hydrolysis by using an enzyme to give an optically active alcohol represented by the following general formula (VII):

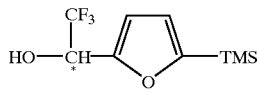

wherein TMS and * have the same meanings as defined above as well as an optically active ester represented by the following general formula (VIIa):

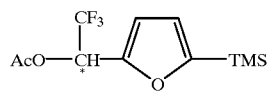

wherein Ac, TMS and * have the same meanings as defined above. As the enzyme to be used in the reaction, various kinds of enzymes can be used so long as each of them is a so called hydrolase, and there may be mentioned, for example, Lipase PS, Lipase MY, Lipase OF, Cellulase, etc. The ester represented by the above general formula (VIIa) can be converted into an optically active alcohol which is in relation of an enantiomer to the alcohol represented by the general formula (VII) by chemical hydrolysis or asymmetric hydrolysis with other enzyme.

Next, the alcohol represented by the general formula (VII) thus obtained is silylated (e.g t-butyl dimethylsilylated) to give a compound represented by the following general formula (VIII):

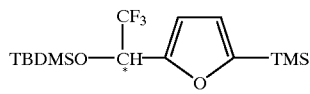

wherein TBDMS, TMS and * have the same meanings as defined above. The reaction can be carried out by using t-butyldimethylsilyl chloride as a silylating agent.

The silyl derivative represented by the general formula (VIII) obtained is oxidized to give a compound represented by the following general formula (IX):

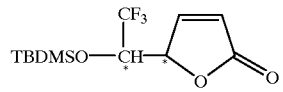

wherein TBDMS and * have the same meanings as defined above. The reaction can be carried out by using an oxidizing agent such as monoperoxyphthalic acid magnesium salt and hydrogen peroxide in a solvent such as acetic acid and chloroform. Also, in this reaction, diastereomer mixtures are obtained, however, these compounds can be easily separated by silica gel column chromatography.

The obtained compound represented by the general formula (IX) is subjected to hydrogenation according to the conventional manner to give a compound represented by the following general formula (X):

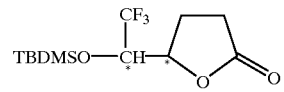

wherein TBDMS and * have the same meanings as defined above. Here, the aforesaid hydrogenation can be carried out by using a solvent such as ethanol, methanol, hexane, ethyl acetate, benzene and toluene, and a catalyst, such as palladium charcoal (Pd/C) in a hydrogen atmosphere.

The obtained lactone derivative represented by the general formula (X) is reduced to give a compound represented by the following general formula (XI):

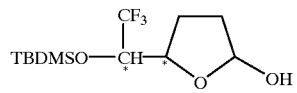

wherein TBDMS and * have the same meanings as defined above. Here, the reaction can be carried out by using a reducing agent such as diisobutylaluminum hydride in a solvent such as diethyl ether and tetrahydrofuran at −20 to −78° C.

Subsequently, the γ-lactol represented by the general formula (XI) thus obtained is treated with a base to give the compound represented by the above-mentioned general formula (II) of the present invention. The reaction can be carried out by using a base such as potassium t-butoxide, in a solvent such as diethyl ether and tetrahydrofuran, at −20 to −78° C.

The aforesaid alcohol compound represented by the general formula (II) is acylated to give a compound represented by the following general formula (XII):

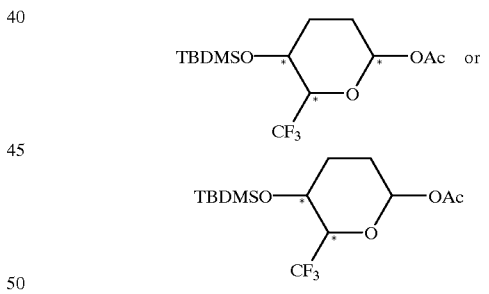

wherein Ac, TBDMS and * have the same meanings as defined above.

The acylation reaction can be carried out by using acetic anhydride, etc., in the presence of a base such as pyridine and toluene, in a solvent such as toluene and methylene chloride, at −50 to 50° C.

Next, when desilylation of the obtained compound represented by the general formula (XII) is carried out, the desired compound represented by the above-mentioned general formula (I) can be obtained. This desilylation reaction can be carried out by using tetra-n-butyl ammonium fluoride as the catalyst in a tetrahydrofuran solvent at 0 to 50° C.

As the representative compound represented by the general formula (I) of the present invention thus obtained, there may be mentioned, for example,

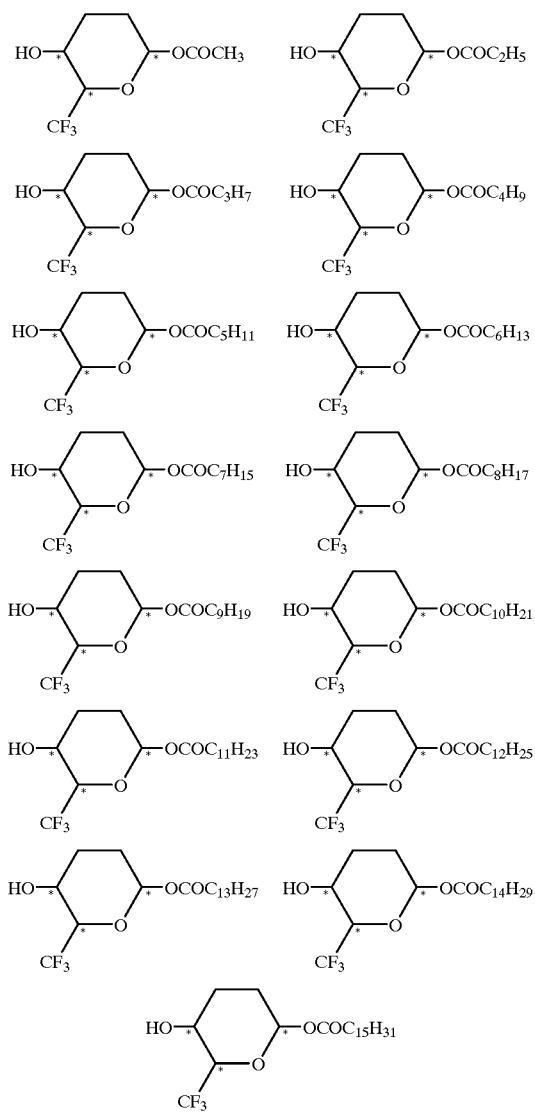

and the like.

According to the present invention, there is obtained a novel compound having a fluoroalkyl group which itself has a large electron attractive property at an asymmetric carbon atom on the tetrahydropyran ring.

These compounds can be expected to find a wide variety of use as raw materials for an enzyme inhibitor, a biologically active substance, an anticancer agent, a ferroelectric liquid crystal, etc.

Next, the present invention will be described in more detail by referring to Examples.

In addition, in the following examples, R and S representation of the optically active compound represented by the general formula (I) of the present invention is carried out based on the positional numbers of the following formula:

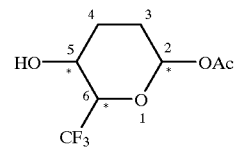

wherein Ac and * have the same meanings as defined above.

EXAMPLE 1

Synthesis of (5#,6#)-tetrahydro-6-trifluoromethyl-2-hydroxy-5-t-butyldimethylsiloxypyran (# represents S or R)

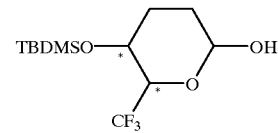

wherein TBDMS and * have the same meanings as defined above.

(a) In a nitrogen atmosphere, 13.6 g (200 mmole) of furan was added to 150 ml of tetrahydrofuran, and 133 ml (200 mmole) of 1.5 mol/liter n-butyl lithium-hexane solution was added dropwise at −20° C. to the mixture and the mixture was reacted for one hour. Subsequently, 21.7 g (200 mmole) of trimethylsilyl chloride was added dropwise to the mixture and the mixture was stirred at −20° C. for one hour. To the mixture was added 133 ml (200 mmole) of 1.5 mole/liter of n-butyl lithium-hexane solution, and after the mixture was reacted at −20° C. for one hour, 28.4 g (200 mmole) of ethyl trifluoroacetate was added dropwise at −78° C. and the mixture was reacted at −78° C. for one hour and at room temperature for further one hour. To the reaction solution was added 3N hydrochloric acid to terminate the reaction and the reaction solution was extracted with ethyl acetate. Subsequently, the extract was washed successively with a saturated sodium hydrogen carbonate aqueous solution and brine, and dried it up with anhydrous magnesium sulfate. Ethyl acetate was distilled away under reduced pressure to give a crude product of a furan derivative.

(b) To 100 ml of dried ethanol was added 2.3 g (60 mmole) of sodium borohydride, and to the mixture was added dropwise the crude product of the furan derivative obtained by the above reaction at 0° C. over a period of 30 minutes. After reaction was carried out at room temperature for 2 hours, ethanol was distilled away under reduced pressure, the reaction was stopped by adding 3N hydrochloric acid and the reaction mixture was extracted with ethyl acetate. Subsequently, the extract was washed successively with a saturated sodium hydrogen carbonate aqueous solution and brine, and dried it up with anhydrous magnesium sulfate. After distilling away ethyl acetate under reduced pressure, vacuum distillation was carried out to obtain 40.5 g (170 mmole) of an alcohol compound.

(c) To 200 ml of methylene chloride were added 23.8 g (100 mmole) of the alcohol compound obtained by the above reaction (b) and 8.9 ml (110 mmole) of pyridine, and to the mixture was added dropwise 8.6 g (110 mmole) of acetyl chloride at 0° C. and the mixture was reacted at room temperature for 12 hours.

Subsequently, the reaction was stopped by adding 3N hydrochloric acid and the reaction mixture was extracted with methylene chloride. Thereafter, the extract was washed successively with a saturated sodium hydrogen carbonate aqueous solution and distilled water, and dried it up with anhydrous magnesium sulfate. After distilling away methylene chloride under reduced pressure, vacuum distillation was carried out to obtain 27.5 g (98 mmole) of an ester compound.

(d) To 1000 ml of distilled water was added 28.0 g (100 mmole) of the ester compound obtained by the above reaction and the mixture was stirred in a mini-jar fermenter at 40° C. To the mixture was added 20 g of Lipase PS and the mixture was reacted for 20 hours. 3N hydrochloric acid was added to the mixture and the mixture was cooled to 0° C. to stop the reaction and filtered with sellaite. The filtrate was extracted with ethyl acetate, after the extract was washed with brine, dried it up with anhydrous magnesium sulfate, and ethyl acetate was distilled away under reduced pressure. Subsequently, the residue was separated and purified by silica gel column chromatography to give 11.7 g (49 mmole) of an optically active alcohol compound and 13.2 g (47 mmole) of an optically active ester compound. The optical purity of the resulting alcohol compound was 97.5% e.e.

(e) In 100 ml of methylene chloride was dissolved 11.7 g (49 mmole) of the optically active alcohol compound obtained by the above reaction. To the solution were added 4.0 g (59 mmole) of imidazole and 8.9 g (59 mmole) of t-butylsilyl chloride at 0° C. and the mixture was stirred for 15 minutes and reacted at room temperature for 16 hours. Distilled water was added to the mixture to stop the reaction, and the reaction mixture was extracted with methylene chloride. Subsequently, the extract was washed with distilled water and dried it up with anhydrous magnesium sulfate. Methylene chloride was distilled away under reduced pressure and the residue was separated and purified by column chromatography to give 16.6 g (47 mmole) of a silyl ether compound.

(f) In a nitrogen atmosphere, to 120 ml of acetic acid were added 14.1 g (40 mmole) of the silyl ether compound obtained by the above reaction and 23.2 g (60 mmole) of magnesium monoperoxyphthalate and the mixture was reacted at 80° C. for 12 hours. After distilling away acetic acid under reduced pressure, a saturated sodium hydrogen carbonate aqueous solution was added to the mixture and the mixture was extracted with ethyl acetate. Subsequently, the extract was washed with brine and dried it up with anhydrous magnesium sulfate. After distilling away ethyl acetate under reduced pressure, the residue was separated and purified by column chromatography to give 4.7 g (16 mmole) of (4S,1'S) butenoride compound and 3.0 g (10 mmole) of (4R,1'S)butenoride compound.

Incidentally, 4.2 g (12 mmole) of the raw material was also recovered.

(g) In 40 ml of ethanol were dissolved, without isolation, 13.7 g (46 mmole) of (4S,1'S) and (4R,1'S)butenoride compounds obtained by the above reaction. To the solution was added 1.4 g of Pd/C (containing 10% by weight of Pd) and the mixture was reacted in a hydrogen atmosphere at room temperature for 15 hours. The reaction mixture was filtered and the solvent was distilled away under reduced pressure, the residue was separated and purified by silica gel column chromatography to give 8.2 g (29 mmole) of (4S, 1'S) butanoride compound and 3.6 g (12 mmole) of (4R, 1'S)butanoride compound.

(h) In a nitrogen atmosphere, to 40 ml of diethyl ether was added 7.5 g (25 mmole) of the (4S,1'S)butanoride compound obtained by the above reaction, and to the mixture was added dropwise 32 ml (30 mmole) of n-hexane solution containing 0.93 mole/liter of aluminum diisobutylhydride at −78° C. and the mixture was reacted for 3 hours. The reaction was stopped by adding distilled water, and after the reaction mixture was neutralized by adding 1N hydrochloric acid, extracted with diethyl ether. After washing the extract with brine, the extract was dried up with anhydrous magnesium sulfate and diethyl ether was distilled away under reduced pressure. Subsequently, the residue was separated and purified by silica gel column chromatography to give 7.3 g (24 mmole) of a lactol compound.

(i) In a nitrogen atmosphere, to 50 ml of tetrahydrofuran was added 7.3 g (24 mmole) of the lactol compound obtained by the above reaction, and to the mixture was added dropwise 10 ml of a tetrahydrofuran solution containing 3.0 g (27 mmole) of potassium-t-butoxide at −78° C. and the mixture was reacted for 3 hours. The reaction was stopped by adding distilled water, after the reaction mixture was neutralized by adding 1N hydrochloric acid, extraction was carried out with diethyl ether. After washing the extract with brine, the extract was dried up with anhydrous magnesium sulfate and diethyl ether was distilled away under reduced pressure. Subsequently, the residue was purified by silica gel column chromatography to give 6.4 g (21 mmole) of (5#,6#)-tetrahydro- 6-trifluoromethyl-2-hydroxy-5-t-butyldimethylsiloxypyran. Though the otabined compound was a diastereomer mixture, the components were not separated from each other.

The physical properties of the compound obtained are shown below.

Molecular formula: $C_{12}H_{23}F_3O_3Si$ $^1H$-NMR (proton nuclear magnetic resonance method):

| δ (ppm) | |
|---|---|
| 0.03 | (s, 6 H) |
| 0.85 | (s, 9 H) |
| 1.40 ~ 2.10 | (m, 4 H) |
| 2.90 ~ 3.10 | (m, 1 H) |
| 3.78 | (dt, J = 5.6, 8.9 Hz, 1 H) |
| 4.11 | (dq, J = 9.2, 6.9 Hz, 1 H) |
| 5.20 ~ 5.40 | (m, 1 H) |
| 0.05 | (s, 6 H) |
| 0.85 | (s, 9 H) |
| 1.40 ~ 2.10 | (m, 4 H) |
| 3.20 ~ 3.40 | (m, 1 H) |
| 3.67 | (dq, J = 8.8, 6.2 Hz, 1 H) |
| 3.70 ~ 3.90 | (m, 1 H) |
| 4.80 ~ 5.00 | (m, 1 H) |

$^{19}F$-NMR (nuclear magnetic resonance method according to isotope fluorine, standard: $CF_3COOH$);

| δ (ppm) | |
|---|---|
| −4.80 | (d, J = 7.6 Hz) |
| −4.90 | (d, J = 6.1 Hz) |

IR (infrared absorption: $cm^{-1}$)
3475, 2975, 2950, 2925, 2875

Mass analysis m/e ($M^+$ + H)
Calculated 301.1447
Found 301.1425

$[\alpha]_D^{23}$ = +55.2° (C (concentration) = 1.00, solvent: chloroform)

EXAMPLE 2

Synthesis of (5#,6#)-tetrahydro-2-acetoxy-6-trifluoromethyl-5hydroxypyran (# represents S or R)

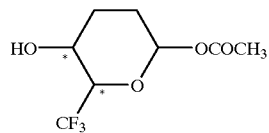

(a) In 3 ml of methylene chloride was dissolved 0.28 g (0.93 mmole) of the pyranose compound obtained in Example 1 (i). To the solution were added 0.11 ml (1.2 mmole) of acetic anhydride and 0.3 ml of pyridine at 0° C., and the mixture was stirred for 15 minutes and reacted at room temperature for 10 hours. To the reaction mixture was added distilled water to stop the reaction and the reaction mixture was extracted with methylene chloride. Subsequently, the extract was washed with distilled water, dried it up with anhydrous magnesium sulfate, and after distilling away methylene chloride under reduced pressure, the residue was purified by column chromatography to give 0.30 g (0.88 mmole) of an acetate compound.

(b) In 3 ml of tetrahydrofuran was dissolved 0.14 g (0.41 mmole) of the acetate compound obtained by the above reaction, and to the mixture was added 0.45 ml of a tetrahydrofuran solution containing 1.0 mole/liter of tetra-n-butylammonium fluoride and the mixture was reacted at 0° C. for 30 minutes and at room temperature for 2 hours. To the reaction mixture was added distilled water to stop the reaction and the reaction mixture was extracted with diethyl ether. Subsequently, the extract was washed with brine and dried it up with anhydrous magnesium sulfate. After distilling away diethyl ether under reduced pressure, the residue was purified by silica gel column chromatography to give 0.08 g (0.37 mmole) of (5#,6#)-tetrahydro-2-acetoxy-6-trifluoromethyl-5-hydroxypyran. Though the obtained compound was a diastereomer mixture, the components were not separated from each other.

The physical properties of the compound obtained are shown below.
Molecular formula: $C_8H_{17}F_3O_4$

| $^1$H-NMR; δ (ppm) | |
| --- | --- |
| 1.60 ~ 2.30 | (m, 4 H) |
| 2.11 | (s, 3 H) |
| 2.29 | (d, J = 3.9 Hz, 1 H) |
| 3.85 | (dq, J = 8.3, 6.3 Hz, 1 H) |
| 3.88 ~ 3.95 | (m, 1 H) |
| 5.78 | (dd, J = 2.4, 8.6 Hz, 1 H) |
| 1.60 ~ 2.30 | (m, 4 H) |
| 2.13 | (s, 3 H) |
| 2.33 | (d, J = 3.4 Hz, 1 H) |
| 3.99 | (dq, J = 9.4, 6.1 Hz, 1 H) |
| 3.88 ~ 3.95 | (m, 1 H) |

-continued

| | |
| --- | --- |
| 6.16 ~ 6.19 | (m, 1 H) |
| $^{19}$F-NMR (standard: $CF_3COOH$); | |
| δ (ppm) | |
| 4.30 | (d, J = 6.2 Hz) |
| IR ($cm^{-1}$) | |
| 3450, 2950, 2875, 1760 | |
| Mass analysis m/e ($M^+$ + H) | |
| Calculated | 229.0687 |
| Found | 229.0658 |
| $[α]_D^{23}$ = −8.8° (C (concentration) = 0.90, solvent: chloroform) | |

What is claimed is:

1. An optically active fluorinated compound represented by the general formula (II):

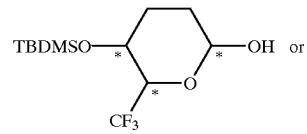

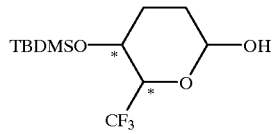

wherein TBDMSO represents a t-butyldimethylsiloxy group and * represents an asymmetric carbon atom.

2. The optically active fluorinated compound of claim 1, having the general formula:

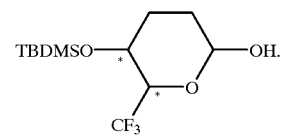

3. The optically active fluorinated compound of claim 1, having the general formula:

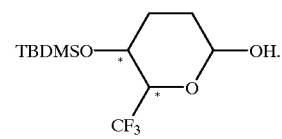

* * * * *